(12) United States Patent
Jones

(10) Patent No.: US 7,175,807 B1
(45) Date of Patent: Feb. 13, 2007

(54) STERILIZATION OF GRIPPING SURFACES

(76) Inventor: Kelly L. Jones, P.O. Box 1178, Columbus, NM (US) 88045

( * ) Notice: Subject to any disclaimer, the term of this patent is extended or adjusted under 35 U.S.C. 154(b) by 0 days.

(21) Appl. No.: 11/299,987

(22) Filed: Dec. 12, 2005

(51) Int. Cl.
*A61L 9/20* (2006.01)
*A61L 2/00* (2006.01)

(52) U.S. Cl. ................. 422/24; 250/455.11; 250/493.1
(58) Field of Classification Search ..................... None
See application file for complete search history.

(56) References Cited

U.S. PATENT DOCUMENTS

| | | |
|---|---|---|
| 2,763,735 A | 9/1956 | Wahl |
| 3,272,927 A | 9/1966 | Peebles |
| 3,314,746 A | 4/1967 | Millar |
| 4,046,508 A | 9/1977 | McDonald |
| 4,710,634 A | 12/1987 | Brookes |
| 5,039,865 A | 8/1991 | Koji |
| 5,314,668 A * | 5/1994 | Biermaier .................. 422/292 |
| 2003/0132279 A1 | 7/2003 | Stemmie |
| 2004/0237255 A1 | 12/2004 | I-Huang et al. |
| 2005/0011042 A1* | 1/2005 | Hupp et al. ................. 16/110.1 |

FOREIGN PATENT DOCUMENTS

| | | |
|---|---|---|
| JP | 07327763 | 12/1995 |
| JP | 2003307049 | 10/2003 |

* cited by examiner

*Primary Examiner*—Nikita Wells
(74) *Attorney, Agent, or Firm*—Rod D. Baker

(57) ABSTRACT

A self-sterilizing gripping or handle apparatus. The apparatus and method of the invention have to do with sterilizing a gripping surface with germicidal ultraviolet light. Embodiments of an apparatus are disclosed which provide for periodic and repeated exposure of a gripping surface to the UV radiation. The gripping surface may be incorporated into a handle, so that the handle remains relatively germ-free between uses by individuals.

40 Claims, 8 Drawing Sheets

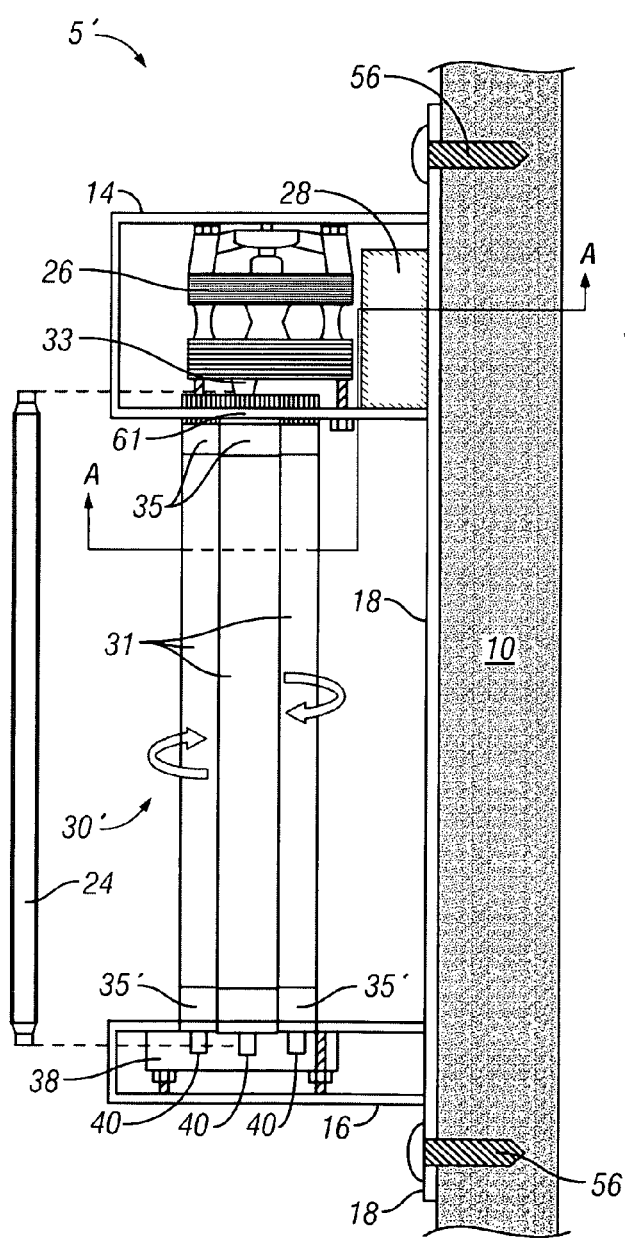
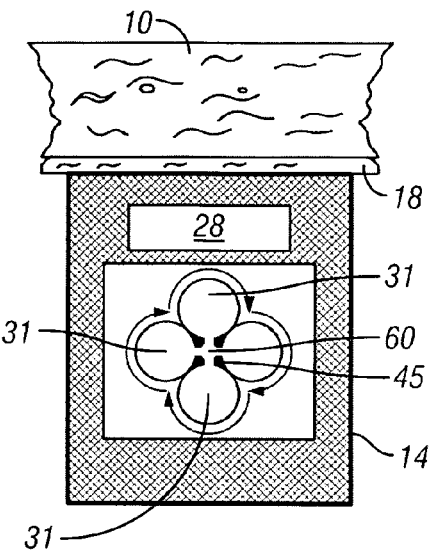
FIG. 3A
FIG. 3
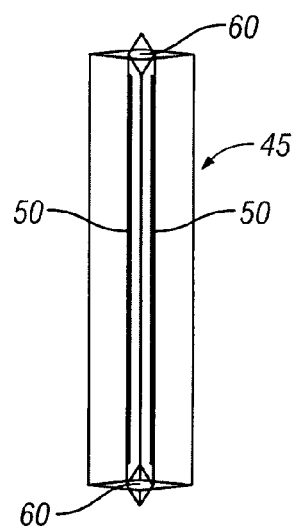
FIG. 3C

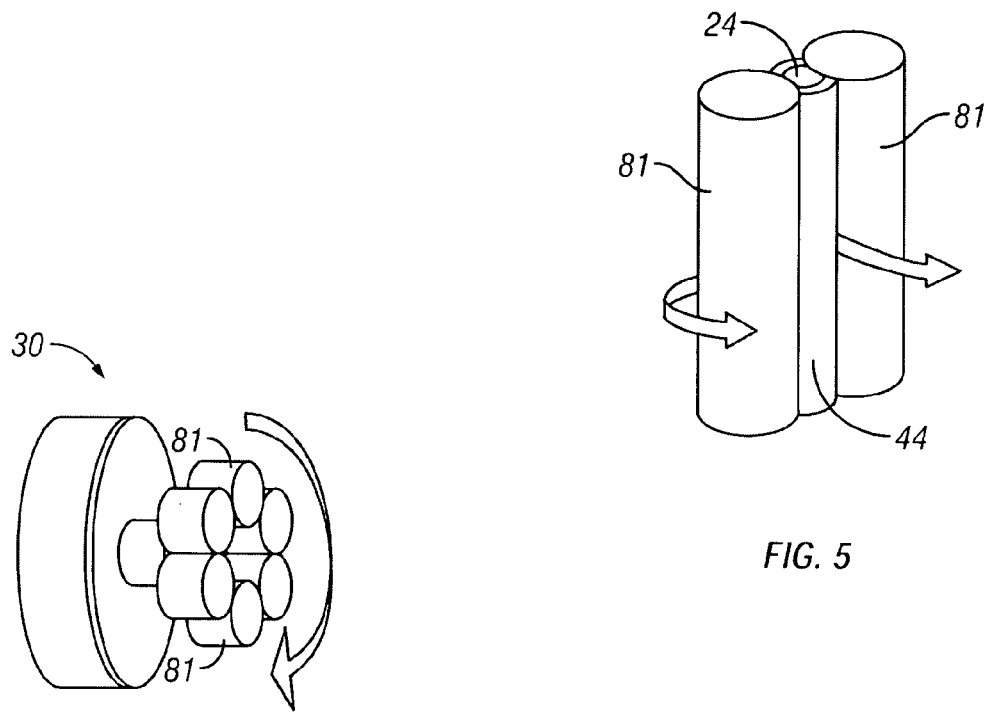
FIG. 5
FIG. 6
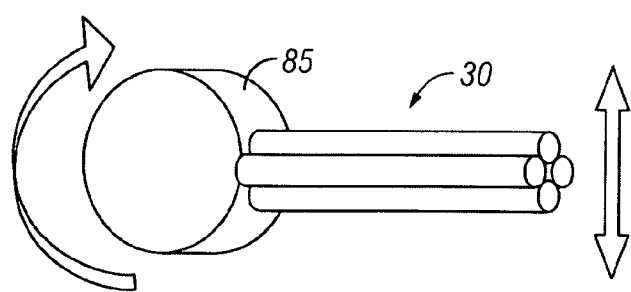
FIG. 7

STERILIZATION OF GRIPPING SURFACES

BACKGROUND OF THE INVENTION

1. Field of the Invention (Technical Field)

The present invention relates to the prevention or control of communicable diseases, and more particularly to a method and apparatus for sterilizing manual gripping surfaces, and specifically to a method and apparatus for sterilizing door handles and knobs.

2. Background Art

Many communicable diseases are transmitted by physical contact between persons, or between a person and surface with which an infected person previously has come in contact. The types and seriousness of communicable diseases transmitted in this manner are varied. Viral and bacterial diseases alike can be communicated by physical contact with surfaces upon which the infectious agents reside. Further, there is an increasing awareness and concern worldwide of the possibility of widespread outbreaks, or even pandemics, of communicable disease; these concerns stem in part from possible spontaneous mutations of influenza and other viruses, as well as the increasing resistance of bacterial strains to conventional and even newly developed and powerful antibiotics.

Consequently, there is a need for improved means for combating the spread of diseases that may be communicated via physical contact with infected surfaces. It has long been known that the frequent washing of one's hands is an effective method for reducing the spread of disease. Perhaps more than any other practice, frequent and thorough washing of the hands may be the preeminent method for avoiding contracting diseases that are contracted by physical contact with infected surfaces (including the hands of other persons, e.g., by way of a friendly handshake).

Also, it is known to apply chemical sanitizers (liquids, atomized sprays, and dry powders) upon surfaces in an effort to disinfect them. Sanitizing hand lotions also are rising in popularity.

Despite the foregoing conventions, there is a problem that a freshly disinfected surface may be, and frequently is, quickly re-contaminated. For example, a person may wash her hand or spray disinfectant on a doorknob, only to have the hand exposed in a handshake with, or the doorknob immediately used by, an infected person with unwashed hands. This problem, which is especially recognized in hospitals, heretofore largely has evaded effective solution.

Perhaps the most commonly encountered infectious surface are gripping surfaces, that is, surfaces of objects that are grasped in the hand for use. Some gripping surfaces are frequently used, often by a wide assortment of persons. The handle or knob of a door perhaps is the best example of a gripping surface that may serve as an intermediary in the spread of communicable disease. Since most doorknobs are used by more than one person, and many doorknobs are frequently used, they are prime candidates for passing infectious agents from one person to another. The handle of a door on a busy public building, for example, may be used by hundreds of different people in a single hour of a business day. Keeping such a handle free from infectious agents is a tremendous challenge.

In this regard, the invention may find focused use in "high contact" vector circumstances, and "high risk" vector circumstances. The high contact handles and knobs are used by vast numbers of different individuals (e.g., front door of a building is handled by 100% of people entering the building, and each subsequent knob is the building is handled by fewer and fewer people as they divert into individual rooms and offices. "High risk" circumstances are handles or knobs unusually likely to bear infectious agents: one of the most obvious targets is public bathrooms.

There have been past efforts to contrive a self-disinfecting handle or knob. Representative past endeavors in this regard, or relating to the general problem described, include the following patents; U.S. Patent Application Publication 2005/0011042 A1 to Hupp et al.; U.S. Patent Application Publication No. 2004/0237255 A1 to Lin et al.; U.S. Patent Application Publication No. 2003/0132279 A1 to Stemmle; U.S. Pat. No. 5,314,668 to Biermaier; U.S. Pat. No. 5,039,865 to Koji; U.S. Pat. No. 4,046,508 to McDonald; U.S. Pat. No. 4,710,634 to Brookes; U.S. Pat. No. 3,314,746 to Millar; U.S. Pat. No. 3,272,927 to Peebles; and U.S. Pat. No. 2,763,735 to Wahl. Also of note are Japanese Patent No. JP2003307049 (publication date 31 Oct. 2003) to Watanabe Yoshisada et al., and Japanese Patent No. JP7327763 (publication date 19 Dec. 1995) to Hashiba Yoshii. However, these known devices and methods are subject to various drawbacks or compromises, including complexity and cost, unreliable disinfection, or exposure of users to dangerous chemicals or radiations.

Against the foregoing background, the present invention was developed.

SUMMARY OF THE INVENTION
(DISCLOSURE OF THE INVENTION)

The apparatus and method of the invention have to do with sterilizing a gripping surface with germicidal ultraviolet light. Embodiments of an apparatus are disclosed which provide for periodic and repeated exposure of a gripping surface to the UV radiation. The gripping surface may be incorporated into a handle, so that the handle remains relatively germ-free between uses by individuals.

A primary object of the present invention is to provide a gripping surface for a handle, for example a door handle that is comparatively free from disease-causing bacteria and viruses.

A primary advantage of the present invention is its effectiveness, reliability, and automatic nature.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 3 is a side sectional view of another desirable embodiment of the apparatus according to the present disclosure;

FIG. 3A is an axial view of the apparatus shown in FIG. 3, taken along section line A—A in FIG. 3;

FIG. 3C is a side view of the shield component of the apparatus shown in FIG. 2A;

FIG. 5 is a top perspective view of an alternative embodiment of the apparatus according to the present disclosure, depicting a handle apparatus similar in overall form and function to the embodiment of FIGS. 3–3C, except employing a pair of cylindrical gripping surfaces disposed on either side of the radiation source;

FIG. 6 is a side perspective view of a rotary door knob incorporating elements and features of the disclosed inventive apparatus; and FIG. 7 is a side perspective view of a horizontal lever-type door handle incorporating elements and features of the disclosed inventive apparatus.

DESCRIPTION OF THE PREFERRED EMBODIMENTS (BEST MODES FOR CARRYING OUT THE INVENTION)

There is disclosed a method and apparatus for ameliorating or preventing the spread of communicable diseases by persons coming in contact with infected gripping surfaces. The concepts and principles of the present disclosure may find application and use in a wide variety of gripping surfaces where it is desired to provide a surface that is relatively free from infectious agents such as viruses or bacteria. "Gripping surface" is the surface of an object that is grasped in the user's hand for use. It is contemplated that the present method and apparatus will be used primarily in the context of building door handles, such as pull or push handles, door knobs and handles separating interior rooms, or even on exterior doors. However, the teachings of this disclosure may find beneficial use in other gripping surfaces, such as cabinet doors, the handles of certain types of tools (such as medical instruments), and the like.

Certain public facilities, especially hospitals, will find ready use of the sanitary handles disclosed herein. Handles and knobs according to the present disclosure may also be used in dormitories, prisons, schools, doctor's offices, and outpatient medical clinics, public bathrooms or other areas where there exists a concern about the spreading of contagious diseases.

The method and apparatus of this disclosure has to do with sanitizing and disinfecting a gripping surface by irradiating the surface with sterilizing ultraviolet light. A key aspect of the disclosure is the movement of the gripping surface past the source of UV radiation to periodically and repeatedly expose the surface to it disinfecting effect. In the preferred embodiments, this movement is accomplished continuously without user supervision, regulation, or actuation. Sterilization of the surface occurs automatically by the operation of the apparatus, and users of the handle may not even be aware of its sterilizing components and functions. Another key benefit to the patent designs is that the sterilization process occurs without exposing the user to the harmful effects of UV radiation. In all embodiments of the disclosed apparatus, the users are protected from direct exposure to UV radiation by the presence of a shield. Thus, the risk of overexposure to intense UV light (particularly to the eyes) is avoided.

Figure 1:
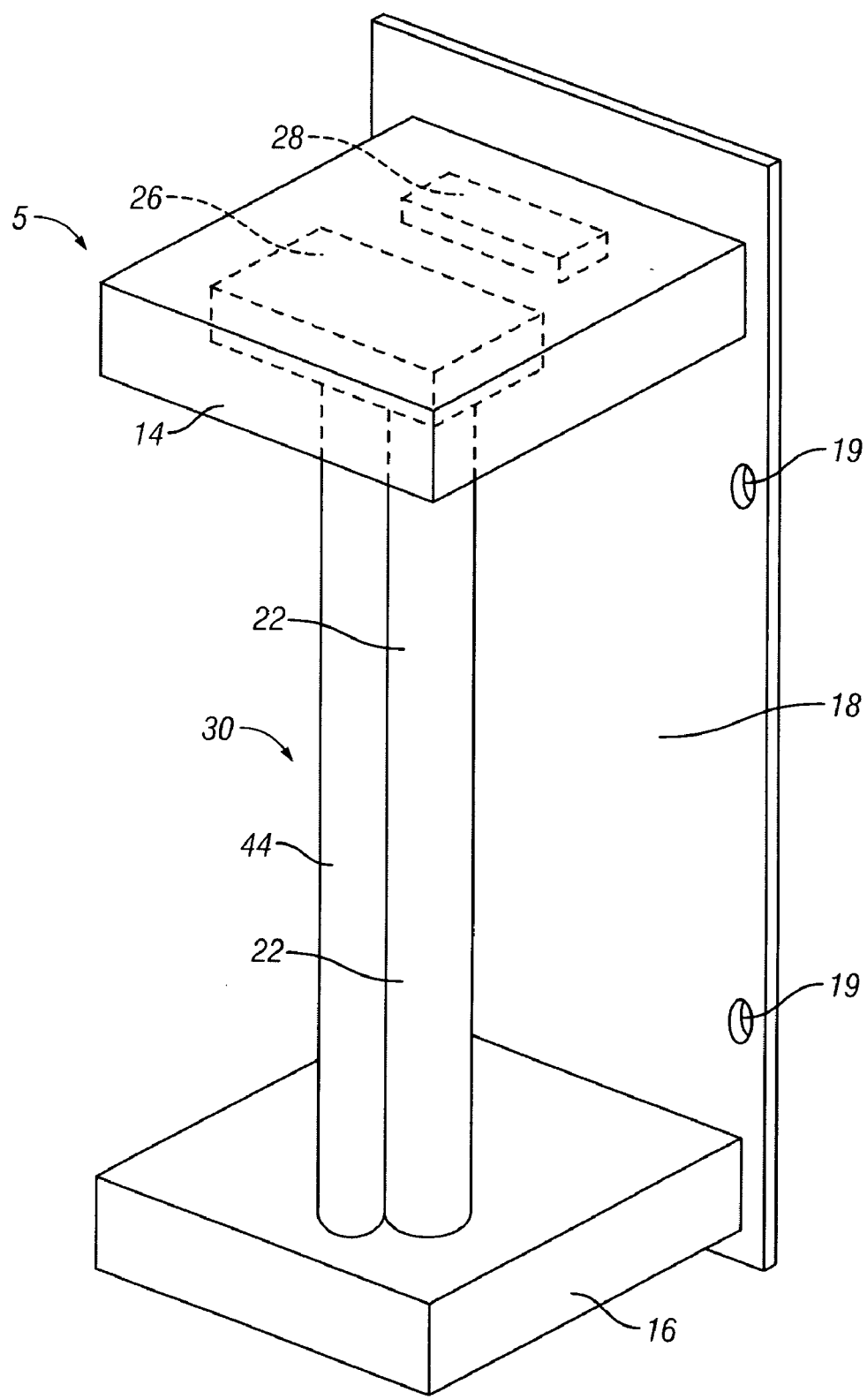
FIG. 1 is a perspective view of one preferred embodiment of a door handle apparatus according to the present disclosure.

Attention is invited to FIG. 1, a perspective view of a preferred embodiment of the present apparatus, and which offers much of its general context and character. The apparatus 5 of the invention is devised for more or less permanent attachment to a door or drawer or the like (not shown in FIG. 1), needing to be opened and closed by a user. The apparatus 5 is depicted in FIG. 1 in a vertical orientation, for example as it might appear when attached to a door. It will be immediately understood, however, that the apparatus 5 may be oriented in any of a wide variety of positions, including horizontal or inclined, in relation to the ground, floor, or other datum.

The apparatus 5 effectively is a handle which may be more or less permanently affixed to the door (or the like) upon which it is to be used. The apparatus 5 requires a source of electrical current (not shown in the figures) for powering its functional elements. Thus, either a battery, or more preferably a source of conventional alternating current, must be present for connection to the apparatus 5. A circuit from the apparatus 5, across the door, and connected to a facility's electrical system may be provided using wiring, switching, and possibly transformers according to generally known principles. Some of these pertinent electrical components may be contained upon the apparatus 5 itself. In alternative possible embodiments, the power source may be a battery contained in the apparatus itself. In such an embodiment, it may be desirable, to prolong battery life, to include in the system a motion sensor and switch to activate the energized components of the apparatus during, and/or for a measured period of time after, the apparatus has been grasped by a user.

The apparatus 5 features a generally rigid and planar back plate 18 which provides structural integrity to the apparatus and by which the apparatus is attached to the door or other object to be sanitarily manipulated. The backplate 18 may be fashioned, for example from stainless steel, and may have screw holes 19 through which screws or nuts may pass for attaching the apparatus 5 to a door.

Extending generally perpendicularly from, and fixedly attached to, the backplate 18 are an upper housing 14 and a lower housing 16 serving to contain and support the functional elements of the apparatus 5. The rigid housings 14, 16 are hollow boxes crafted, for example, from steel plates or other suitable composition. In the preferred embodiment, a rigid, cylindrical gripping surface 22 extends from the upper housing 14 to the lower housing 16. Gripping surface 22, which in the preferred embodiment is defined by comparatively lightweight, yet strong, steel tube, is rotatably mounted at its ends to the housings 14, 16, such that the cylinder may rotate around its axis. Notwithstanding that the gripping surface 22 cylinder is rotatable about its axis, its physical connection to the housings 14, 16 is secure against lateral displacement, so that a user may open a door to which the apparatus 5 is attached by grasping and pulling (or pushing) the gripping surface (or, in alternative embodiments, twisting (rotating), or by pressing the handle up, down, in, or out).

Immediately adjacent and parallel to the gripping surface 22 is a tubular radiation shield 44, whose configuration and function will be further described. The shield 44 is strong and rigid, and also extends between the two housings 14, 16. A source of germicidal UV radiation (not visible in FIG. 1) is housed within the shield 44; UV radiation emitted from within the shield 44 impinges upon the gripping surface 22 as it rotates. The gripping surface 22 and the shield 44 in an auxiliary role serve as a handle 30.

It is noted that in this and all embodiments of the disclosed apparatus, there is provided the advantage of locating the UV radiation source in close proximity to the griping surface. In this and all other embodiments of the apparatus, the UV radiation source 24 is situated, for example from about 0.125 to about 1.0 inches from the portion gripping surface 22 being irradiated. Typically, both the gripping surface 22 and the radiation source 24 have axial lengths, and are mounted parallel to each other by a separation distance that is as small as practicable. This reduced distance of separation offers advantages of more reliable sanitization (than if radiation source was more remote), as well as the ability to achieve results with comparatively reduced-wattage sources. Low-powered radiation sources are both safer and less expensive to operate over time.

One of the housings, as shown in FIG. 1 the upper housing 14, contains an electric motor 26. The motor 26 is operatively connected to the gripping surface 22 thereby to rotate the gripping surface at a preselected rate when the motor is running. Either of the housings 14, 16 (in the figures, the upper housing 14) also houses the necessary ballast 28 for the UV radiation source, typically an ultraviolet lamp. The housing 14 may also contain all or most of the means (gears, or belts, etc.) for periodically moving a portion of the gripping surface 22 past the UV radiation source contained within the shield 44.

Figures 2, 2A:
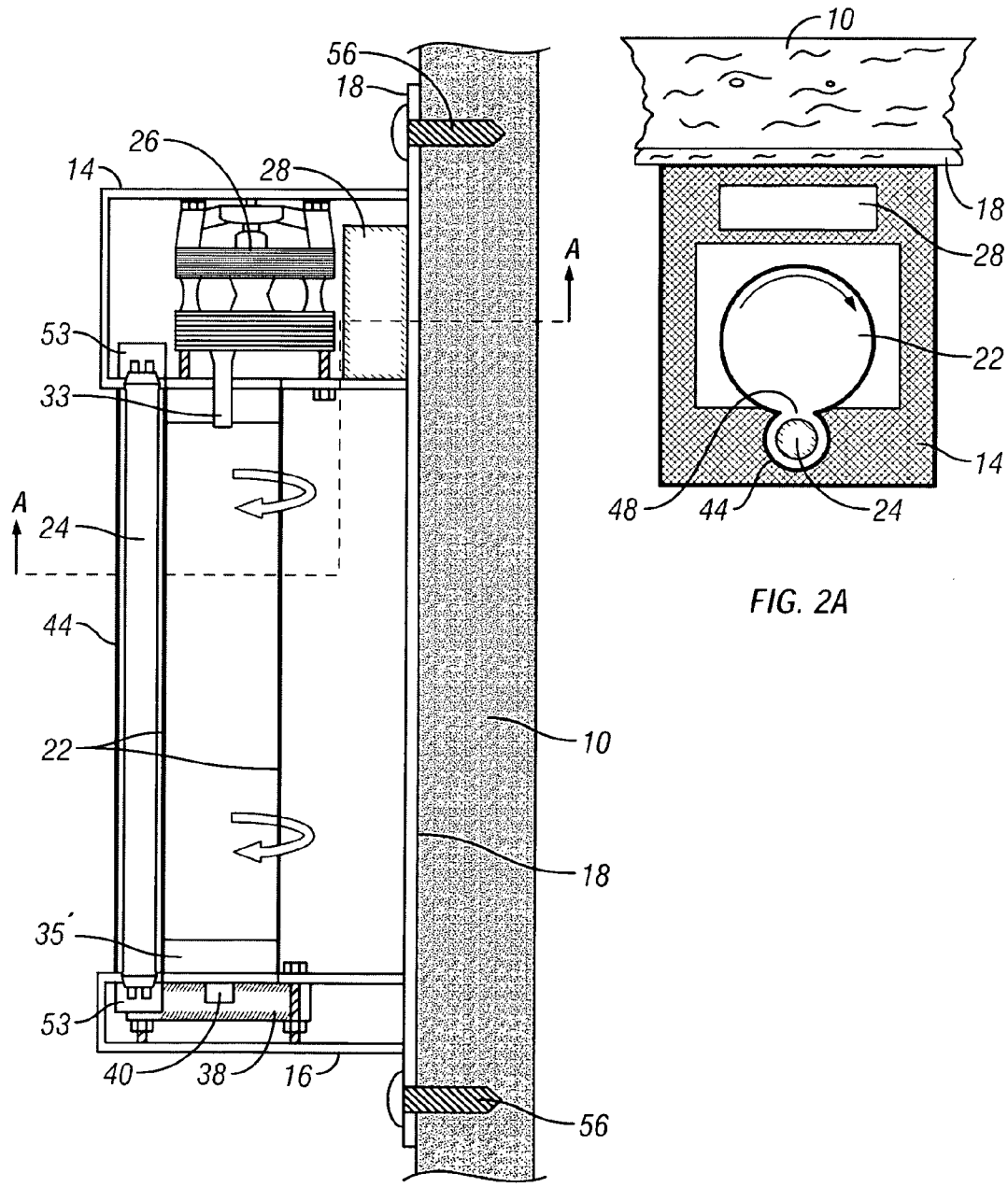
FIG. 2 is a side sectional view of the apparatus shown in FIG. 1.
FIG. 2A is an axial sectional view of the apparatus shown in FIG. 1, taken along section line A—A in FIG. 2A.
Figure 2B:
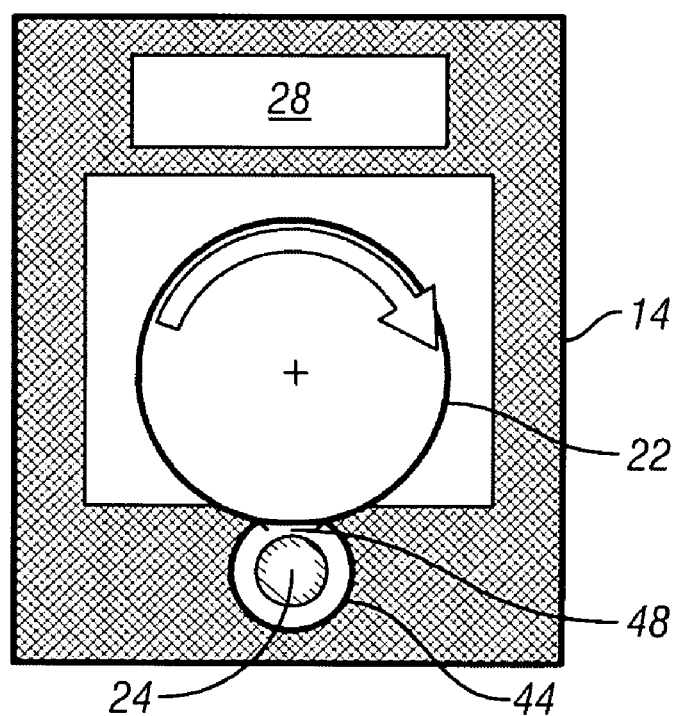
FIG. 2B is the view of FIG. 2A enlarged to better illustrate details of the apparatus seen in FIG. 1.

Combined reference is made to FIGS. 2–2B, showing further detail of the preferred embodiment seen in FIG. 1. The apparatus 5 as shown in FIG. 2 is securely mounted upon the door 10 by means, for example, of door bolts 56 disposed through the backplate 18 and into the body of the door, generally in accordance with methods used in conventional handles. The backplate 18 is flush against the body of the door 10.

The gripping surface 22 which preferably defines, or is in the shape of, a cylinder extends between the upper housing 14 and lower housing 16. As mentioned, a portion of the gripping surface 22 is contactable by a user's hand when the user grasps the apparatus 5. That is, the user wraps his fingers around the gripping surface 22 (and perhaps also contacts the UV shield 44 incidentally) in order to push or pull the apparatus 5, for example to open a door 10. Thus, the cylindrical gripping surface 22 in the preferred embodiment primarily defines a handle 30.

The cylindrical gripping surface 22 is, for example, a stainless steel tube having a smooth or even polished finish. As seen in FIG. 2, the gripping surface tube has end caps 35, 35' within its ends to promote strength of the component and provides structure whereby the tube is connected to the respective housings 14, 16. FIG. 2 illustrates that a bearing mounting plate 38 may be secured, by nuts and bolts or the like, to the lower housing 16. A bearing 40 connected to the lower end cap 35' extends into and rotates within the bearing mounting plate 38. Accordingly, the lower end of the gripping surface tube is free to rotate in relation to the mounting plate 38, yet the bearing's engagement with the plate 38 prevents the lower end of the gripping surface tube 22 from shifting radially. In a preferred embodiment seen in FIG. 2, the drive shaft 33 of the motor 26 is fixedly attached to the upper end cap 35. When the motor 26 is actuated, its rotary power is imparted to the gripping surface 22 via the drive shaft 33. The drive shaft 33 also effectively serves as the other bearing for the gripping surface tube, securing the tube against any but axial rotation.

Reference is made to FIGS. 2 and 2A. A source of UV radiation 24, most typically an elongated, commercially available UV lamp, is disposed in proximity to the gripping surface 22. In all embodiments of the present apparatus, the preferred source of UV radiation is a lamp 24. The lamp 24 or other suitable UV radiation source emits radiation having a wavelength of between approximately 240 nm and approximately 280 nm, more preferably a wavelength of about 254 to 263 nm, and 253 nm being desirable. Ultraviolet radiation in this range of wavelengths is known to be germicidal. Germicidal UV is also called UV-C or shortwave UV, and is between 240 and 280 nm with 254–263 nm being the most effective at killing germs (i.e. breaking down DNA). Lamps suitable for many of the applications of the present disclosure are known and available commercially, or may be custom manufactured (e.g., in reduced or miniature sizes) according to principles known in the art. The UV lamp 24 is removably attached within the apparatus by means of conventional electrical contact sockets 53.

A shield 44 is disposed around the radiation source 24. The shield 44 has an aperture 48 therein, through which radiation may pass, the aperture 48 being closely adjacent to the gripping surface 22. As seen in FIGS. 1–2B, the shield 44 may be a tube, with the aperture 48 being a longitudinal slot defined in and through the wall of the tube shield 44. It is seen that the tubular shield 44 is situated substantially parallel to the handle 30, with the slot 48 confronting the most proximate portion of the gripping surface 22. As best seen in FIG. 2A, the slot 48 is located on an imaginary plane defined by the central axes of the cylinder of the handle 30 and the tubular shield 44.

The positional relationship between the cylindrical gripping surface 22, the tubular radiation shield 44, and the radiation aperture or slot 48 is best seen in FIG. 2B, which is an enlarged view of these components. The radiation source 24 emits ultraviolet radiation radially in all directions outward. The shield 44 however, safely blocks and contains such radiation, preventing it from escaping the apparatus 5. However, the aperture 48 in the shield 44 permits the germicidal radiation to pass from within the shield and to irradiate the adjacent, rotating cylindrical gripping surface 22. The lamp ballast 28 allows for the powering up of the UV lamp 24 in accordance with convention.

There is provided a means for periodically moving at least a portion of the gripping surface 22 past the UV radiation source. This means for periodically moving ordinarily is the electric motor 26, which is in operative connection with the gripping surface 22. The operative connection between the motor 26 and the gripping surface 22 may be any suitable mechanical means for transferring the motor's power to impart rotary motion to the cylindrical gripping surface 22. In the previously mentioned example, the motor's driveshaft 33 may be connected directly to the handle 30 at its axis; alternatively, there may be a series of gears and cogs, or pulleys and continuous belts, whereby the rotary motion of the motor's driveshaft 33 is transferred to the handle 30. By the rotating motion of the handle 30, the gripping surface 22 is repeatedly exposed to the UV radiation emitted by the UV source 24.

FIGS. 2, 2A and 2B all have directional arrows illustrating the rotation of the gripping surface according to the function of the apparatus. The motor 26 (and any associated gears, etc.) is operated to drive the rotation of the gripping surface at a suitable, predetermined rate. The gripping surface's rate of rotation is selected and optimized so that any given portion (e.g. a longitudinal strip) of the gripping surface 22 passes by the radiation aperture 48 with a frequency effectively to maintain the sterility of the total gripping surface. By way of illustrative example, the gripping surface 22 may rotate at around 1.0 rpm; in such a case, the entire gripping surface is irradiated every minute; such an irradiation frequency may suffice to prevent the gripping surface from communicating infection between users, especially if the gripping surface is used, on the average, less than one time per minute. It will immediately be understood that the rate of rotation for the gripping surface 22 may be determined and effectuated according to context. Factors to be considered include how often the gripping surface is used, the relative need for careful prevention of the communication of infectious agents (i.e., in the ICU or surgical operating room of a hospital), and the electricity budget. The rate of rotation has an upper limited that is established, as a practical matter, by the discomfort a user feels when grasping a rotating handle surface. Nevertheless, in most or all applications and environments, the diameter of the cylindrical gripping surface, and the rate of its rotation, can be established within parameters permitting comfortable use of the gripping surface 22 while also irradiating the entire gripping surface with effective frequency. The gripping surface's rate of rotation affects the rate of exposure that bacteria (and the like) has to the UV light—preferably, a surface should be exposed for at least eight seconds in order for the most germs to be sterilized. (Different germs have different exposure requirements). Additionally, UV radiation is cumulative; therefore, if an infectious microbe is exposed for 50% of the time needed during a first rotation of the gripping surface, the next rotation or exposure will complete the sterilization process.

Attention is invited to FIGS. 3–3C, illustrating an alternative embodiment of the disclosed apparatus. This embodiment of the apparatus 5' is similar in most respects and functions to the embodiment previously described, and like numerals are used to identify like components in FIGS. 1–2B and FIGS. 3–3C. The principal difference between this alternative embodiment and the embodiment of FIGS. 1–2B is that the handle 30' of this first alternative is constructed of a plurality of parallel adjacent cylindrical gripping surfaces, rather than the single cylinder 22 of FIGS. 1–2B. In this embodiment, an array of cylindrical "subsurfaces" 31 constitutes the overall gripping surface of the handle 30'; the number of cylinders is at least two, and preferably four as depicted in FIGS. 3 and 3A. An even number (e.g., four or six) of these cylinders 31 may be preferred, as an even number of cylinders may be arranged contiguously so that adjacent cylinders 31 are in rolling contact with each other, if desired. (It is well known that having three contiguous cylinders in mutual rolling contact is mechanically impossible, as one of the cylinders is forced but unable to rotate in opposite directions instantaneously.) It is preferable, nevertheless, that the rotating cylinders or shafts should all rotate in the same direction to prevent a finger or other material from being pulled accidentally into the center of the handle.

Accordingly, in the alternative embodiment of FIGS. 3–3C, the gripping surface is effectively provided or configured from an array of three (or in alternative embodiments more than three) parallel cylinders 31 equidistantly arranged around an imaginary central axis. Each individual cylinder 31 is journaled between the upper and lower housings 14, 16 similarly to the rotatable mounting described for the preferred embodiment of FIGS. 1 and 2. Each cylinder has a bearing 40 rotationally engaged into the bearing plate 38, while the upper or opposite end of each cylinder 31 is rotatably attached to the upper housing 14 in any suitable manner providing for operative connection with the motor 26. Properly assembled, therefore, the apparatus 5' permits for separate rotation of each cylinder about its own axis. The plurality of cylinders 31 in the array effectively may define a handle 30' such as the handle of a door. The UV lamp 24 or other UV radiation source is disposed within a specially configured shield 45 along the axis thereof, and the shield in turn is located on the imaginary central axis about which the array of cylinders 31 is radially symmetrically arranged.

Tangential portions (i.e. i.e. longitudinal strips so narrow as practically to define lines) of adjacent cylinders preferably are posed extremely close together, or may even be placed in rolling contact. The cylinders 31 surround radially an axial interior space in which the shield 45 (and the UV source 24 contained therein) is situated, while the cylinders themselves also effectively serve as blocks or screens of the radiation that otherwise might escape the array. The outside surfaces of the plurality of cylinders collectively define a lobed, very generally cylindrical, overall gripping surface which functions as a gripping handle. Thus, when the apparatus 5' of this embodiment is in use, the user reaches around and grasps all the cylinders 31 to push or pull the apparatus 5'. Both the cylinders 31 and the shield 45 impede the UV light from escaping.

The safety of this embodiment is enhanced by the use of the shield 45 which further assures that no potentially harmful UV radiation escapes the apparatus from between adjacent cylinders 31. The shield 45 is disposed within the array of cylinders 31, substantially coaxial with the array's central axis. The UV radiation source 24, which preferably is an off-the-shelf generally cylindrical germicidal UV lamp, is within the hollow interior of the shield 45.

Figure 3B:
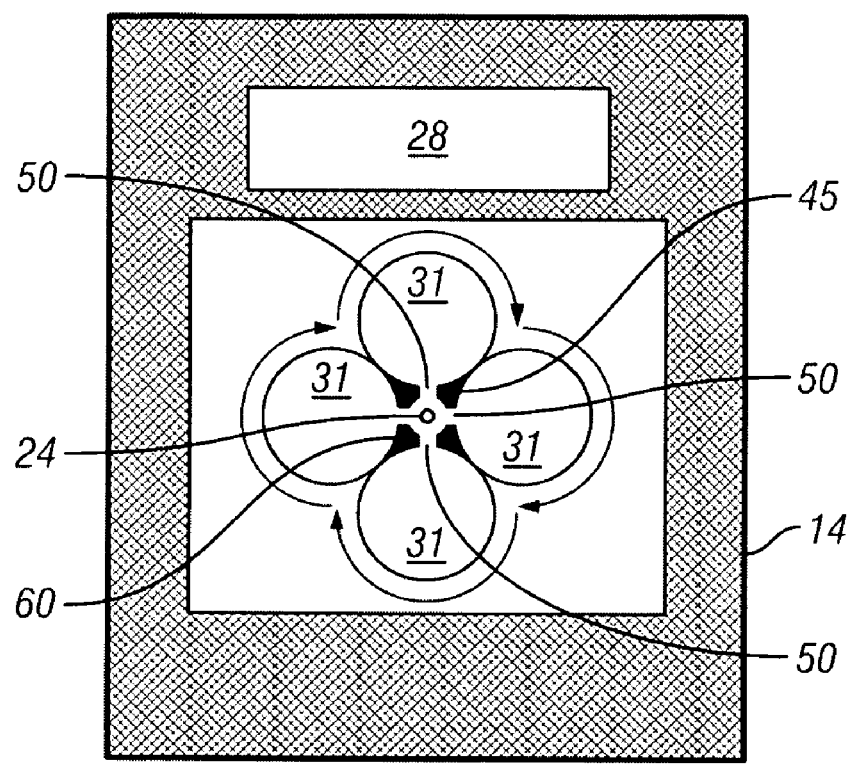
FIG. 3B is the view of FIG. 3A enlarged to better illustrate details of the apparatus seen in FIG. 3.

Referring especially to FIGS. 3A–3C, it is seen that the fluted shield 45 has, in radial cross section, a florafoil or lobed rosette-like shape. The number of petals or lobes equals the number of cylinders 31, and the shield is placed within the array so that the lobes extend radially outward into corresponding spaces between cylinders 31, as best seen in FIG. 3B.

A shield 45 for use within an apparatus 5' having four cylinders 31 is depicted in isolation in FIG. 3C. The shield 45 has a central conduit 60 in which the long cylindrical lamp 24 is located in a fully assembled apparatus 5'. The shield 45 also features a plurality of apertures 50 therein, through which radiation may exit the interior of the shield to irradiate the outsides of the cylinders 31. Preferably, the number of the radially arrayed radiation apertures 50 corresponds to the number of cylinders 31, so that there is an aperture 50 adjacent to each one of the cylinders, as indicated in FIG. 3B. As already suggested hereinabove, the shield 45 may be in the general shape of a rigid tube; in such an instance the apertures 50 in the tube shield preferably are longitudinal slots defined in and through the wall of the shield at the intersections of adjacent lobes thereof (FIG. 3C). As evident from the figures, the tubular shield 45 ideally is disposed substantially parallel to the cylinders 31, with the slot apertures 50 located on imaginary planes defined by the central axis of the array of cylinders 31 and the respective axes of the cylinders themselves (FIG. 3B).

Continued reference is made to FIGS. 3–3C, collectively. Most preferably in this embodiment, the array of cylinders 31 substantially encloses the axial interior space 58 in which the UV radiation source 24 is located. According to the foregoing, the shield 45 is specially shaped in radial cross section substantially to fill the portion of this axial interior space 58 that is radially between the UV radiation source 24 and the cylinders 31. Being thus configured, the shield 45 prevents passage of radiation between adjacent ones of the cylinders 31, and thus eliminates a potential user hazard.

In the embodiment of FIGS. 3–3C, there is provided a suitable power take-off from the motor's drive shaft 33 to each one of cylinders 31 thereby to rotate individually the cylinders. Any suitable gear train set 61, or other operative linkages such as belts and pulleys or the like, thus allow the motor 26 to drive the cylinders 31, to rotate them in appropriate coordinated directions. As suggested by the broad directional arrows in FIGS. 3, 3A and 3B, in one version the cylinders 31 of a four-cylinder array do not quite contact each other and thus may all rotate in the same direction (clockwise as viewed in FIG. 3A). Rotating the cylinders in a uniform direction may be mechanically expedient; alternatively, adjacent pairs of cylinders in the array may rotate in opposite directions, permitting adjacent cylinders to be in rolling contact (again, provided there is an even number of cylinders).

Figures 4, 4A:
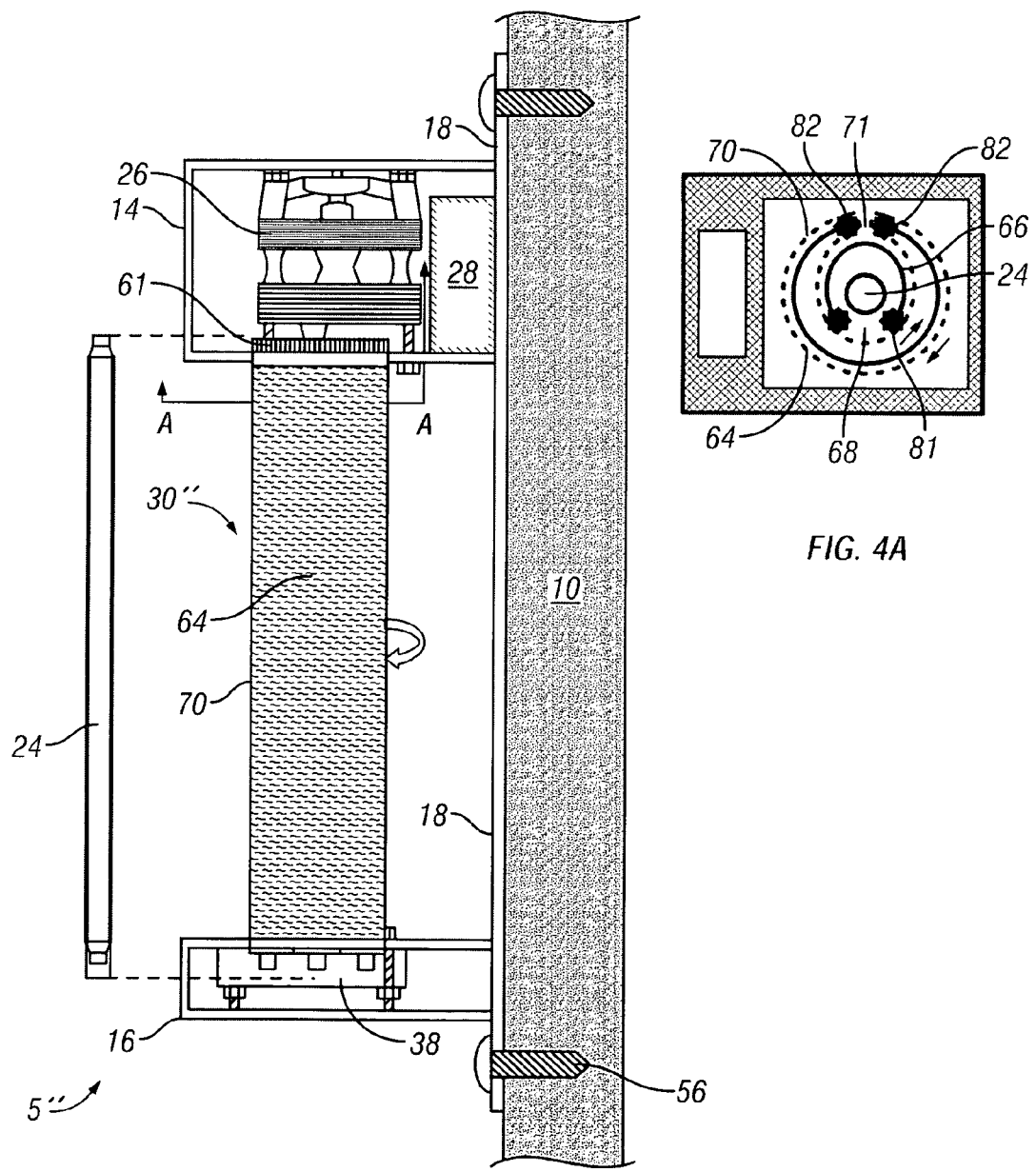
FIG. 4 is a side sectional view of yet another alternative embodiment of the apparatus according to the present disclosure.
FIG. 4A is an axial view of the apparatus shown in FIG. 4, taken along section line A—A in FIG. 4.
Figure 4B:
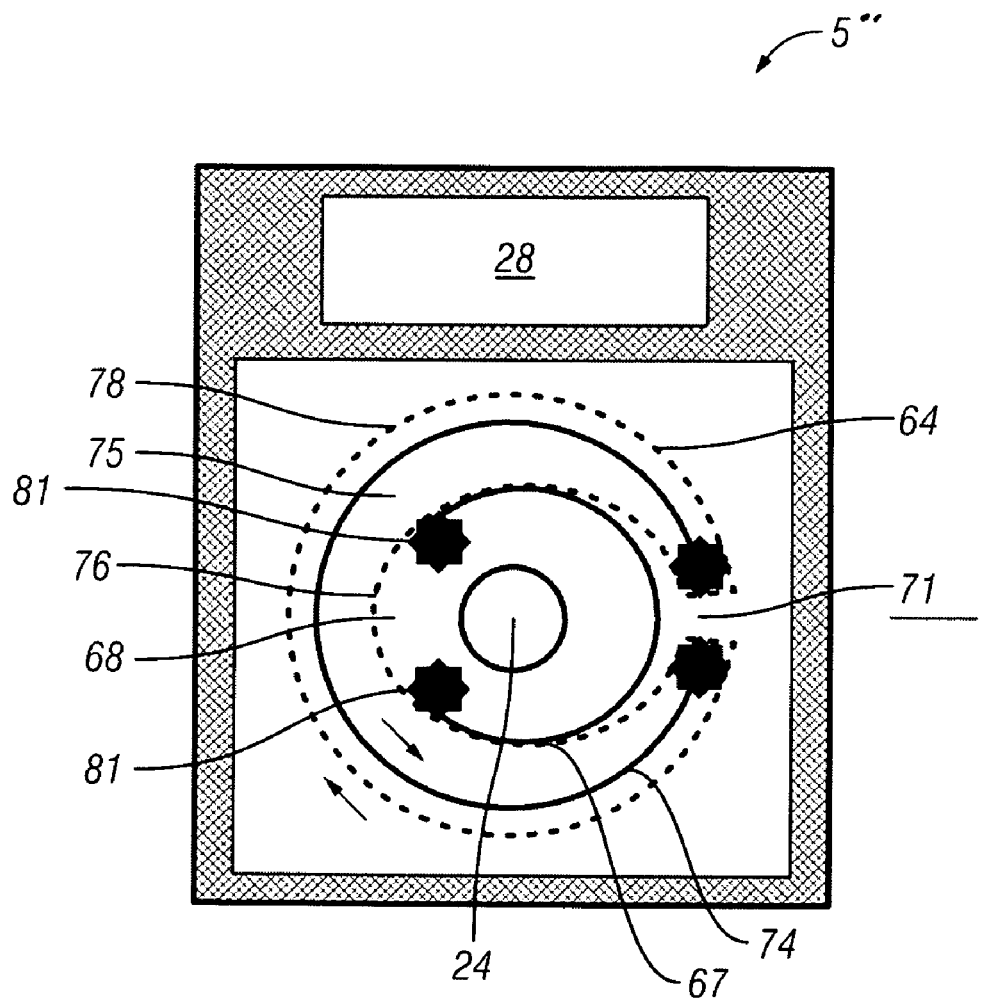
FIG. 4B is the view of FIG. 4A enlarged to better illustrate details of the apparatus seen in FIG. 4.

Attention may now be turned to FIGS. 4–4B, which disclose yet another alternative embodiment of the apparatus. This embodiment is a departure from the previously described embodiments. Many components are common to all embodiments, however, and like numerals again are used to identify like elements common to all the drawing figures. This embodiment is somewhat more elaborate, and uses a continuous, belt-like flexible sheet as the main gripping surface, rather than the exterior surfaces of rigid cylinders as disclosed in previous embodiments.

Described generally, this third alternative embodiment surrounds the UV radiation source with two co-axial cylinders. The inner one of these two cylinders is a rigid tube that functions as the primary radiation shield. The outer cylinder, which also is a rigid tube, functions as the secondary shield and also as a housing upon which the sheet-like gripping surface may slidably move. The outer housing has a longitudinal slot therein which permits the flexible sheet-like gripping surface to be wrapped around the housing to be substantially adjacent to both its inner surface and outer surface. The inner shield also has a longitudinal slot defined therein which functions as the radiation port, whereby germicidal radiation escapes from inside the shield to irradiate the sheet-like gripping surface as it moves past the port. The sheet is engaged with sprockets, or has frictional contact with rollers or the like, at least some of which in turn are powered by the electric motor to drive the sheet, in a continuous belt-like manner, in a serpentine path around and between the inner shield and outer housing. As a consequence of the sheet's movement, incremental portions thereof move past the germicidal radiation source, thus periodically sterilizing the entirely of the outer surface of the sheet (with which the user comes in contact).

Thus the gripping surface comprises a flexible tubiform sheet 64, which is moved past the UV radiation source 24 to be periodically exposed to its germicidal effects. The sheet 64, which defines a continuous elongated belt-like loop, is fashioned from any suitably flexible and durable material capable of prolonged UV radiation exposure, and may be, for example, selected from metal fabrics, textile fabrics, polymers or fine chain mails or screens. A fine chain mail or highly flexible screen is preferred. It is preferred that the sheet 64 be bendable, i.e., freely and mostly non-elastically distortable out-of-plane, but that it not be significantly stretchable in-plane (a characteristic, for example, of a fine chain mail).

Referring to FIGS. 4–4C, there is seen a tubular shield 66 disposed around the radiation source 24. The inner shield 66 has a smooth outer surface 67 generally cylindrical in its contour. The inner shield 66 has defined in and through its wall at least one radiation aperture 68, through which radiation may pass from the interior to the exterior of the shield. The aperture 68 may be an axial line of closely spaced circular openings through the shield, but preferably is a single, narrow, longitudinal slot.

A tubular housing 70 is disposed coaxially around the shield 66, the latter having the comparatively smaller diameter. The housing 70 and shield 66 extend between the upper and lower housings 14, 16, and are well-secured thereto, similar to previously described embodiments. The housing 70 has an outer surface 74 which, like the inner shield's outer surface 67, defines a smooth cylinder. The housing 70 has an opening 74 therein, preferably a longitudinal slot through the housing wall, through which the flexible sheet 64 may be moved. As best seen in FIG. 4A, this opening 74 is radially offset in relation to the radiation aperture 68 in the shield 66. Because the outer surface 67 of the inner shield, and the outer surface 74 of the housing have a fine finish, the sheet 64 may slide or ride across these surfaces in flush or conforming contact with them. The housing 70 and the sheet 64 wrapped thereon effectively constitute in combination a handle 30" for gripping by the user of the apparatus.

There is an intermediate space 75 defined between the inner shield 66 and the housing 70. As best seen in FIG. 4C, the sheet 64 is folded to define an inner loop 76 within an open outer loop 78; the sheet thus is wrapped around the housing 70 and through its opening 74. So folded and arranged, the inner loop 76 of the sheet 64 is disposed in the intermediate space 75, and the outer loop 78 is placed into sliding contact with the outer surface 74 of the housing 70. In this manner, the gripping surface sheet 64 is serpentinely movable into and out of the housing's opening 74, and simultaneously past the radiation aperture 68 in the shield 66.

Referring especially to FIGS. 4B and 4C, rollers or sprockets 81 are rotatably mounted at or near the longitudinal edges of the shield 66 defining the slot-like radiation aperture 68. Likewise, rollers or sprockets 82 rotatably disposed at the edges of the housing 70 which define its slot opening 71. Preferably, the toothed sprockets 81, 82 (or rollers) are long and rod-like to extend the full axial lengths of the aperture 68 and opening 71 respectively. The sprockets 81 on the shield 66 promote smooth sliding passage of the sheet 64 along the shield's outer surface 67 and past its radiation aperture 68. The sprockets 82 on the housing 70 define the lines of flexure for the sheet as it abruptly bends around the edges of the opening 71, thus facilitating the movement of the sheet 64 through the opening. Also, at least one of the sprockets 82 on the housing 70 has powered rotation, and possible one or more of sprockets 81 likewise, as described further herein.

In this alternative embodiment, the means for periodically moving the relevant portion of the sheet that is the gripping surface, past the UV radiation source 24 is somewhat more elaborate than in previously described embodiments. As in previous embodiments, the gripping surface (the sheet 64) is driven by an electric motor 26. However in this embodiment the sprockets 81, 82 are engaged with the sheet 64, with the electric motor 26 in operable connection (for example, via gear trains or drive belts) with at least one of the sprockets 81 or 82 to rotate it (them). Alternative means for moving the sheet 64 may be provided, for example the sheet may have operable and frictional contact with a set of cylindrical rollers in lieu of sprockets 81, 82.

Actuation of the motor 26 thus causes a driven sprocket or sprockets (or roller(s)) to rotate to drive the sheet 64 as indicated by the directional movement arrows in FIGS. 4B and 4C. The sheet moves continuously through the intermediate space 75 and past the radiation aperture 68 where it is exposed to its germicidal effects. Notably and as most evident from an inspection of the drawing figures, the inner surface of the sheet's inner loop 76 faces radially inward toward the UV source 24 and thus is directly exposed to its sterilizing rays. However, as the sheet moves along in its serpentine manner, the "inner surface" of the sheet's inner loop 76 becomes the "outer surface" of the outer loop 78 each time the sheet topologically is "flipped" or inverted by passage around the two outer sprockets 82. The sterilized surface of the sheet thus is the radially outward-facing gripping surface with which a user's fingers and palm come in contact.

Concurrently and further, it is seen that the sheet 64 moves continuously slidably past and along the outside surface 71 of the housing 70. The sheet lies flush against the outside surface 74 and the user of the apparatus grips the sheet 64 between her hand and the housing 70 in order to open the door, drawer, or the like. The sheet 64 moves at a rate slow enough that its movement, although perhaps perceptible beneath the grasp of the user, does not interfere with the handle function of the apparatus.

Because the opening 71 in the UV-opaque housing 70 is offset radially from the radiation aperture 68 in the shield (180° offset seen in the drawing figures), there is no possibility of radiation inadvertently escaping the interior of the apparatus 5". The apparatus thus is safe for uses on doors, drawers, cabinets, and the like in ordinary use.

The use and utility of the apparatus is apparent from the foregoing, but is now summarized. As a result of their continual rotation or sliding movement, the gripping surfaces 22, 31, 64 of the various embodiments are periodically and repeatedly moved past the source of germicidal UV radiation. The gripping surface is radiated in incremental portions, but continuous movement is at a speed adequate to sterilize the entire gripping surface over the course of a selected predetermined time interval, for example from one to five minutes. As a result, there is a tremendously decreased possibility that the gripping surface will be the incubator or repository of infectious agents for extended periods of time. The gripping surface is comparatively sterile, and may function as a handle without also functioning as a primary point of disease contact and contraction for users.

It also is evident from the foregoing that the apparatus may be configured variously to meet the objectives of the invention without departing from the scope thereof. For example, FIG. 5 illustrates that a handle may incorporate a pair of rotating cylinders 81, 81' disposed on generally opposite (but not necessarily diametrically opposite) sides of a slotted tubular shield 44' situate around the elongated radiation source 24. This embodiment is generally similar in all respects to the embodiment of FIGS. 3–3C, except as to the number of cylinders and the shape of the shield 44'. FIG. 5 serves to illustrate that the number of rotating cylinders (directional arrows in FIG. 5 indicate direction of powered rotary motion) and the shape of an intermediate radiation shield can be adopted and varied tremendously without departing from the scope of the invention.

Referring to FIG. 6, it is seen that a number of individually rotating cylinders 81 (six seen in FIG. 6) can be mounted and arrayed to define a larger cylindrical gripping surface, with an interiorly located and shielded UV radiation source (generally in accordance with the embodiment of FIGS. 3–3C) to serve as the handle more closely approximating the rotary-activated latches commonly encountered, especially in homes and offices. The overall handle 30 is actuated by rotating it in the ordinary manner, as suggested by the directional arrow in the figure.

Door handles in institutional settings, such as industrial plants, laboratories, public buildings and the like often have lever-type actuation whereby the latch mechanism is actuated by a levered pivoting action as opposed to rotation. FIG. 7 illustrates that the principles of the present disclosure may be embodied in a lever handle 30 mounted upon a pivoting base 85, whereby the user pushes down or up on the gripping surface of the handle 30 to activate the latch, as suggested by the directional arrow in FIG. 7.

The apparatus may be actuated and left to function largely unattended. With a constant and reliable electricity source to supply the motor and UV radiation source, the apparatus is essentially automatic in nature, and sterilizes the gripping surface continually, twenty-four hours a day, 365 days year, if desired. Bearings and gears may require occasional lubrication, and the UV lamp may require removal and replacement from time to time, but the durable apparatus with proper maintenance offers reliable service for many years with only modest maintenance needs.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

I claim:

1. A self-sterilizing gripping apparatus comprising:
    a gripping surface, a portion of said gripping surface being contactable by a user's hand when the user grasps the apparatus;
    a source of UV radiation disposed in proximity with said gripping surface; and
    means for periodically moving said portion of the gripping surface past said UV radiation source;
    wherein said portion of said gripping surface is repeatedly exposed to UV radiation.

2. An apparatus according to claim 1 wherein said gripping surface comprises a cylinder.

3. An apparatus according to claim 2 wherein said cylinder defines a door handle.

4. An apparatus according to claim 1 further comprising a shield disposed around said radiation source, said shield having an aperture therein through which radiation may pass, said aperture being closely adjacent to said gripping surface.

5. An apparatus according to claim 4 wherein said shield comprises a tube having a longitudinal slot therein, said tube being disposed substantially parallel to said handle, with said slot confronting the most proximate portion of said gripping surface.

6. An apparatus according to claim 5 wherein said slot is located on an imaginary plane defined by central axes of said cylinder and said tube.

7. An apparatus according to claim 1 wherein said gripping surface comprises an array of at least two parallel cylinders equidistantly arranged around a central axis.

8. An apparatus according to claim 7 wherein at least three cylinders define a door handle.

9. An apparatus according to claim 8 further comprising a shield disposed within said array substantially coaxial with said central axis, said radiation source situate within an interior of said shield, said shield having a plurality of apertures therein through which radiation may exit said interior to irradiate said cylinders.

10. An apparatus according to claim 9 wherein the number of said apertures corresponds to the number of said cylinders, an aperture being adjacent to each of said cylinders.

11. An apparatus according to claim 9 wherein said shield comprises a tube having longitudinal slots therein, said tube being disposed substantially parallel to said cylinders with said slots located on imaginary planes defined by the central axis and the axes of said cylinders.

12. An apparatus according to claim 9 wherein said array of cylinders substantially encloses an axial interior space in which said UV radiation source is disposed, and wherein further said shield substantially fills a portion of said axial interior space radially between said UV radiation source and said cylinders, thereby to prevent passage of radiation between adjacent ones of said cylinders.

13. An apparatus according to claim 1 wherein said gripping surface comprises a flexible tubiform sheet.

14. An apparatus according to claim 13, further comprising:
  a tubular shield disposed around said radiation source, said shield comprising an outer surface, and said shield defining a radiation aperture therein through which radiation may pass;
  a tubular housing disposed coaxially around said shield, said housing comprising an outer surface, and said housing defining an opening therein through which said flexible sheet may be moved, said opening being radially offset in relation to said radiation aperture;
  there being an intermediate space defined between said shield and said housing;
wherein said sheet is folded to define an inner loop within an open outer loop, said sheet wrapped around said housing and through said opening;
wherein said inner loop is disposed in said intermediate space and said outer loop is in sliding contact with said outer surface of said housing; and
wherein said sheet is serpentinely movable into and out of said opening and past said radiation aperture.

15. An apparatus according to claim 14 wherein said housing and said sheet comprise a handle.

16. An apparatus according to claim 15 wherein said sheet comprises a member selected from the group consisting of metal fabrics, textile fabrics, polymers and fine chain mails.

17. An apparatus according to claim 15 said means for periodically moving said portion of the gripping surface past said UV radiation source comprises:
  sprockets engageably connected to said sheet; and
  an electric motor in operable connection with said sprockets to rotate said sprockets;
wherein when said sprockets are rotated by said motor, said sheet moves continuously through said intermediate space past said radiation aperture; and wherein further said sheet moves continuously slidably past and along said outside surface of said housing.

18. An apparatus according to claim 1 wherein said UV radiation source is an ultraviolet lamp.

19. An apparatus according to claim 1 wherein said UV radiation source emits radiation having a wavelength of between approximately 240 nm and approximately 280 nm.

20. An apparatus according to claim 19 wherein said UV radiation source emits radiation having a wavelength of about 253 nm.

21. An apparatus according to claim 1 wherein said means for periodically moving said portion of the gripping surface past said UV radiation source comprises an electric motor in operable connection with said gripping surface.

22. A self-sterilizing handle comprising:
  a handle having a gripping surface, a portion of said gripping surface being contactable by a user's hand when the user grasps the handle;
  a source of UV radiation disposed in proximity with said handle; and
  means for periodically moving said portion of the gripping surface past said UV radiation source;
wherein said portion of said gripping surface is repeatedly exposed to UV radiation.

23. An apparatus according to claim 22 wherein said UV radiation source emits radiation having a wavelength of between approximately 240 nm and approximately 280 nm.

24. An apparatus according to claim 23 wherein said UV radiation source emits radiation having a wavelength of about 253 nm.

25. An apparatus according to claim 22 wherein said means for periodically moving said portion of the gripping surface past said UV radiation source comprises an electric motor in operable connection with said gripping surface.

26. An apparatus according to claim 23 wherein said gripping surface of said handle defines a cylinder.

27. An apparatus according to claim 26 further comprising a shield disposed around said radiation source, said shield having an aperture therein through which radiation may pass, said aperture being closely adjacent to said gripping surface.

28. An apparatus according to claim 27 wherein said shield comprises a tube having a longitudinal slot therein, said tube being disposed substantially parallel to said handle, with said slot confronting the most proximate portion of said gripping surface.

29. An apparatus according to claim 28 wherein said slot is located on an imaginary plane defined by central axes of said cylinder and said tube.

30. An apparatus according to claim 23 wherein said gripping surface comprises an array of at least two parallel cylinders equidistantly arranged around a central axis.

31. An apparatus according to claim 30 further comprising a shield disposed within said array substantially coaxial with said central axis, said radiation source situate within an interior of said shield, said shield having a plurality of apertures therein through which radiation may exit said interior to irradiate said cylinders.

32. An apparatus according to claim 31 wherein the number of said apertures corresponds to the number of said cylinders, an aperture being adjacent to each of said cylinders.

33. An apparatus according to claim 32 wherein said shield comprises a substantially tubular member, and said apertures comprise longitudinal slots in said tubular member, said tube being disposed substantially parallel to said cylinders with said slots located on imaginary planes defined by the central axis and the axes of said cylinders.

34. An apparatus according to claim 33 wherein said array of cylinders substantially encloses an axial interior space in which said UV radiation source is disposed, and wherein further said shield is configured in radial cross-section to substantially fill a portion of said axial interior space radially between said UV radiation source and said cylinders, thereby to prevent passage of radiation between adjacent ones of said cylinders.

35. A self-sterilizing handle comprising:
- a gripping surface, a portion of said gripping surface being contactable by a user's hand when the user grasps the handle;
- a source of UV radiation disposed in proximity with said gripping surface; and
- an electric motor operably associated with said gripping surface;

wherein said motor moves said portion of the gripping surface past said UV radiation source, thereby repeatedly exposing said portion of said gripping surface to UV radiation.

36. An apparatus according to claim 35 wherein said UV radiation source emits radiation having a wavelength of between approximately 240 nm and approximately 280 nm.

37. An apparatus according to claim 36 wherein said gripping surface of said handle defines a cylinder.

38. An apparatus according to claim 37 further comprising a shield disposed around said radiation source, said shield having an aperture therein through which radiation may pass, said aperture being closely adjacent to said gripping surface.

39. An apparatus according to claim 38 wherein said shield comprises a tube and said aperture comprises a longitudinal slot in said tube, said tube being disposed substantially parallel to said gripping surface, with said slot confronting the most proximate portion of said gripping surface.

40. An apparatus according to claim 39 wherein said slot is located on an imaginary plane defined by central axes of said cylinder and said tube.

* * * * *